United States Patent
Lizotte-Waniewski et al.

(10) Patent No.: US 6,268,153 B1
(45) Date of Patent: Jul. 31, 2001

(54) POLYMERASE CHAIN REACTION DIAGNOSTIC ASSAYS FOR THE DETECTION OF DIROFILARIA IMMITIS IN BLOOD AND MOSQUITOES

(76) Inventors: Michelle Lizotte-Waniewski, 64 Hawley St., #1, Northampton, MA (US) 01060; Steven A. Williams, 65 Depot Rd., North Hatfield, MA (US) 01066

( * ) Notice: Subject to any disclaimer, the term of this patent is extended or adjusted under 35 U.S.C. 154(b) by 0 days.

(21) Appl. No.: 09/581,493
(22) PCT Filed: Dec. 18, 1998
(86) PCT No.: PCT/US98/27063
    § 371 Date: Jun. 14, 2000
    § 102(e) Date: Jun. 14, 2000
(87) PCT Pub. No.: WO99/32504
    PCT Pub. Date: Jul. 1, 1999

Related U.S. Application Data
(60) Provisional application No. 60/071,792, filed on Dec. 19, 1997.

(51) Int. Cl.$^7$ .................................................. C12Q 1/68
(52) U.S. Cl. ................................ 435/6; 435/5; 435/252.1; 435/252.3; 435/91.1; 435/91.2
(58) Field of Search ................................ 435/5, 6, 252.1, 435/252.3, 91.1, 91.2

(56) References Cited

PUBLICATIONS

Haddock, (1987), "Canine Heartworm Disease: A Review and Pilot Study," Soc. Sci. Med., 24(3): 225–246.

Knight (1987), "Heartworm Infection," Vet. Clin. North Am. Small Anim. Pract., 17(6); 1463–1518.

Monchy et al. (1993), "Pulmonary Dirofilriasis," Med. Trop. (Mars.), 53(3); 366–371.

Ro et al. (1989), "Pulmonary Dirofilariasis: The Great Imitator of Primary or Metastatic Lung Tumor. A Clinico-pathologic Analysis of Seven Cases and a Review of the Literature," Hum. Path., 20(1); 69–76.

Riley et al. (1992), "Development of a Polymerase Chain Reaction–based Diagnosis of Trichomonas vaginalis," J. Clin. Microbiol., 30(2); 465–472.

Wesley et al. (1997), "Application of Multiplex Polymerase Chain Reaction for Rapid Identification of Campylobacter jejuni and C. coli Associated with Reproductive Failure," Am. J. Vet. Res., 58(10); 1070–1075.

Guadagnino et al., (1997), "Prevalence, Risk Factors, and Genotype Distribution, of Hepatitis C Virus Infection in the General Population; A Community–based Survey in Southern Italy," Hepatology, 26(4); 1006–1011.

Kowalchuk et al. (1997), "Detection and Characterization of Fungal Infections of Ammophila arenaria (Marram Grass) Roots by Denaturing Gradient Gel Electrophoresis of Specifically Amplified 18S rDNA," Appl. Environ. Microbiol., 63(10); 3858–3865.

Kuan (1997); "Detection and Rapid Differentiation of Human Enteroviruses Following Genomic Amplification" J. Clin. Microbiol., 35(10); 2598–2601.

*Primary Examiner*—W. Gary Jones
*Assistant Examiner*—Janell E. Taylor
(74) *Attorney, Agent, or Firm*—Fitch, Even, Tabin & Flannery

(57) ABSTRACT

The present invention discloses polymerase chain reaction (PCR) based assays for the presence of the heartworm parasite *Dirofilaria immitis* prevalent in dogs and cats, as well as in mosquitoes, which are the transmission vector. The assays are extremely sensitive, and can be used effectively to screen large numbers of samples. The invention provides primers and kits for use in the PCR assay of the invention which are oligonucleotides or oligonucleotide derivatives specific for *D. immitis*. The invention further discloses methods of detecting the presence of *D. immitis* in a sample based on PCR which employs the primers of the invention. The invention also discloses methods for rapidly obtaining parasite DNA from blood samples and mosquitoes. The samples that may be assayed include blood samples from mammals (especially dogs and/or cats) suspected of harboring *D. immitis* and mosquitoes suspected of transmitting the pathogen.

34 Claims, 4 Drawing Sheets

Figure 1

| Primer Pairs | SEQ ID NO.: | | PRIMER SEQUENCE |
|---|---|---|---|
| Primary 5S PCR Pair: (5S-rDNA) | 1 | Forward: | 5' - GTTAAGCAACGTTGGGCCTGG - 3' |
| | 2 | Reverse: | 5' - TTGACAGATCGGACGAGATG - 3' |
| Nested 5S-sp PCR Pair: (5S spacer) | 3 | Forward: | 5' - CAAGCCATTTTCGATGCACT - 3' |
| | 4 | Reverse: | 5' - CCATTGTACCGCTTACTACTC - 3' |
| NCR PCR Pair: (noncoding repeat) | 5 | Forward: | 5' - GATAGATTGATCGCAAGTAC - 3' |
| | 6 | Reverse: | 5' - GAAGATTTTGAGTATGATGAG - 3' |

POLYMERASE CHAIN REACTION DIAGNOSTIC ASSAYS FOR THE DETECTION OF DIROFILARIA IMMITIS IN BLOOD AND MOSQUITOES

This application is a 371 of PCT US98/27063 filed Dec. 18, 1998 which claims benefit of Ser. No. 60/071,792 filed Dec. 19, 1997.

FIELD OF THE INVENTION

The present invention relates to methods of detecting the presence of the pathogenic parasite, *Dirofiliaria immitis,* in host mammals such as dogs and cats, as well as in the transmission vector (i.e., mosquitoes). The methods are based on polymerase chain reaction-based amplification of *Dirofiliaria immitis*-specific DNA sequences. This present invention also relates to methods for treating mammalian (including human) blood samples.

BACKGROUND OF THE INVENTION

Dog heartworm disease and, to a lesser extent, cat heartworm disease due to infection by *Dirofiliaria immitis* is a significant problem in the United States and world-wide. (See Haddock (1987), "Canine Heartworm Disease: A Review and Pilot Study," *Soc. Sci. Med.,* 24(3): 225–246; Knight (1987), "Heartworm Infection," *Vet. Clin. North Am. Small Anim. Pract.,* 17(6); 1463–1518; Monchy et al. (1993), "Pulmonary Dirofilariasis," *Med. Trop. (Mars.),* 53(3); 366–371; Ro et al. (1989), "Pulmonary Dirofilariasis: The Great Imitator of Primary or Metastatic Lung Tumor. A Clinicopathologic Analysis of Seven Cases and a Review of the Literature," *Hum. Path.,* 20(1); 69–76.) Infection begins when infective larvae (third stage—L3) from an infected mosquito are deposited on the skin of the animal. The infective larvae enter through the bite wound and burrow into the subcutaneous tissue. During the next two to four months, larvae will molt twice to become immature adult worms. The immature adult worms penetrate veins to enter the bloodstream and then migrate to the right side of the heart where they will continue to mature into adult worms. Once they become sexually active (generally about six to seven months post-infection), they will produce first stage microfilariae (i.e., L1 or active embryos) which will circulate in the bloodstream. The microfilariae require a mosquito host to further develop. While feeding, a mosquito will ingest microfilariae along with its blood meal. The microfilariae picked up by the mosquito change from the first stage to the infective third stage (L3) in about 10–30 days, depending on ambient temperatures, and then migrate to the mosquito's mouth parts where they can be injected into a new host animal, thereby completing the *Dirofiliaria immitis'* life cycle.

In infected animals, the adult worms (up to 10 to 12 inches in length) generally occur in the right heart chambers and associated vessels and can live up to six to seven years. Microfilariae (first stage larvae) can live in the bloodstream up to about three years. Visible symptoms (e.g., labored breathing, coughing, and unexplained exhaustion) from the disease are usually observed only in chronically infected dogs and cats, considerable damage to heart, lung, and kidney function can occur before symptoms are generally observed. Treatment (i.e., intravenous injections of an adulticide such as thiacetarsamide followed after about four to six weeks with a microfilaricide such as dithiazanine) can be effective (especially with early diagnosis of the infection). Such treatment, however, is generally expensive since hospitalization is recommended and, in some cases, forced rest for a prolonged period may be required. In some cases, the treatment may need to be repeated. Moreover, the treatment is not without risk to the animal since killed heartworms and/or microfilariae can result in blood clots which can lodge in, for example, the lungs. In many cases, especially in advanced cases where chronic symptoms are already evident at the time of diagnosis, the disease can be fatal even with treatment because of the increased risk of blood clots and other complications. In such advanced cases or where the animal cannot withstand the chemical treatment method, surgery may be necessary to remove the adult heartworms. Thus, prevention of the initial infection is a much preferred alternative since it is both safer and significantly less expensive. Although the risk of an initial infection can be significantly reduced by keeping pets indoors, this is not a viable alternative for many (and perhaps most) pet owners; moreover, infection can occur through the bite of a single infected mosquito. Administration of a prophylactic agent such as diethylcarbamazine on a daily basis or Ivermectin on a monthly basis to at-risk animals throughout the mosquito season (and several months thereafter) can be very effective in preventing the initial infection. Such preventive treatments should only be begun, however, once it is confirmed that no microfilariae are present in the blood since the treatment itself can cause serious problems, including death, in already infected animals. Even when using a preventive program, periodic testing for *D. immitis* is still recommended to insure the program is working properly and to detect any infection that may have been present, but not detected, before treatment began.

Ideally, all dogs and cats (both pets and strays) should be tested for the presence of *D. immitis,* preferably on a periodic basis. As noted above, such a test is especially important if the specific animal is to be placed on a regimen with a prophylactic agent to prevent infection. If *D. immitis* is detected in a given population, appropriate measures can be taken to eliminate the parasite in the affected animals and/or, if appropriate, to institute the appropriate preventive treatment in the yet-uninfected animals and otherwise limit the spread of the parasite.

Direct observation of microfilariae in the blood using a microscope can be used. The accuracy of this method, however, is substandard since adult heartworms may be present even in the apparent absence of microfilariae (e.g., only worms of one sex may be present; adult worms may be sexually immature or too old to reproduce; the concentration may be too low; or the animal's immune system may be successful in destroying the microfilariae). In addition, direct microscopic evaluation for mass screening of a large population of animals would be expensive due to the time and skill levels required for such individual evaluations. Currently the most accurate test available for screening blood samples for *D. immitis* in dogs is an antigen test. (This antigen test is not effective in cats.) Since this immunoassay appears to mainly detect the presence of the adult worm, it does not have the specificity and/or sensitivity required to detect infection by the parasite throughout its life cycle. This could be a problem if, for example, the antigen which is the analyte in this immunoassay were not found at a high level in all the larval stages and in the adult. Thus, there remains a need for an assay which is specific for *D. immitis,* is highly sensitive to the presence of the parasite in a host, and has the ability to detect *D. immitis* regardless of the stage in the life cycle the parasite may be in at the time of sampling. Moreover, there is a need for an assay which is relatively quick and easy to perform and which can, therefore, be used for general screening of the dog and/or cat population in a given location.

Currently there is no known assay that is useful for detecting the parasite in the mosquito vector. Nevertheless knowledge of the geographic extent and density of *D. immitis* in the vector population is an important factor in planning eradication programs. One must know where parasite-bearing mosquitoes are found, and veterinary authorities should be able to assess the geographic distribution of susceptible dogs and cats. Thus there is a clear need for an assay directed at the mosquito vector which is specific for *D. immitis*, and sensitive enough to detect the parasite in a single or small number of mosquitoes that may be harvested in the field. As in the case of an assay in samples from dogs and cats, an assay carried out on mosquito samples should be able to detect *D immitis* at any stage its life cycle within the mosquito.

The sensitivity and specificity of DNA-based assays in detecting bacterial, viral, and parasite DNA in clinical samples has been demonstrated. (See Riley et al. (1992), "Development of a Polymerase Chain Reaction-based Diagnosis of *Trichomonas vaginalis*," *J. Clin. Microbiol.*, 30(2); 465–472; Wesley et al. (1997), "Application of Multiplex Polymerase Chain Reaction for Rapid Identification of *Campylobacter jejuni* and *C. coli* Associated with Reproductive Failure," *Am. J. Vet. Res.*, 58(10); 1070–1075; Guadagnino et al., (1997), "Prevalence, Risk Factors, and Genotype Distribution, of Hepatitis C Virus Infection in the General Population; A Community-based Survey in Southern Italy," *Hepatology*, 26(4); 1006–1011; Kowalchuk et al. (1997), "Detection and Characterization of Fungal Infections of *Ammophila arenaria* (Marram Grass) Roots by Denaturing Gradient Gel Electrophoresis of Specifically Amplified 18S rDNA," *Appl. Environ. Microbiol.*, 63(10); 3858–3865; Kuan (1997), "Detection and Rapid Differentiation of Human Enteroviruses Following Genomic Amplification," *J. Clin. Microbiol.*, 35(10); 2598–2601.) There remains, however, a need for the development of a rapid, accurate, relatively inexpensive DNA-based assay for *D. immitis* in both host (i.e., dog and/or cat) and vector (i.e., mosquito) species. The present invention provides such a DNA-based assay.

SUMMARY OF THE INVENTION

The present invention provides a polymerase chain reaction-based (PCR-based) assay for the presence of the heartworm parasite *D. immitis* prevalent in dogs and cats (or other mammals). Because the assay is extremely sensitive, it can be used effectively to screen large numbers of dog and cat blood samples in a reasonable time period and at a reasonable cost. Additionally, it can be used to monitor the effectiveness of treatment regimes in animals found to be infected. The assay is also intended for use by epidemiologists to document the transmission level of this parasite by monitoring parasite burden in the mosquito vector population. Data regarding the parasite burden can be used to develop, and/or monitor the effectiveness of, eradication programs. Such data may also provide early warning of the risk of heartworm disease in areas currently free of the parasite so that appropriate preventive measures can be implemented. Prior to the present invention, the detection of *D. immitis* in the mosquito vector was only possible by the individual dissection and microscopic examination of the mosquito.

The present PCR-based assays were developed using repeated DNA sequences cloned and sequenced from the heartworm parasite *D. immitis*. Specific PCR primers were designed to amplify these repeated DNA sequences found in the parasite genome. The specific PCR primers designed for use in this invention are illustrated in FIG. 1. The repeated DNA sequences used to design the primer sets are illustrated in FIGS. 2 and 3. Using the procedures of this invention, test samples (either blood samples from potentially infected dogs and/or cats or dried mosquito samples from potentially infected vectors) are processed to digest proteins and liberate parasite DNA, if present. The *D. immitis* parasite DNA is then detected using the *D. immitis* repeat-specific primers in the polymerase chain reaction. Only those samples containing parasite DNA give a positive signal when the PCR results are visualized using, for example, agarose gel electrophoresis. This assay can detect less than about one attogram ($10^{-18}$ grams) of *D. immitis* DNA, which corresponds to less than one microfilaria in 1 ml of blood, or less than one L3 larva in about fifty mosquitoes. Moreover, this assay can detect *D. immitis* infection for all life cycle stages of the parasite. Although the present method is especially suitable for testing blood samples from dogs and cats, it can also be used with blood samples from other mammals, including humans.

The primers for use in the PCR assay of the invention are oligonucleotides or oligonucleotide derivatives specific for *Dirofiliaria immitis*. The specific primers developed for use in this invention are included in FIG. 1. These specific primer pairs include: (1) SEQ ID NO.: 1 and SEQ ID NO.: 2—the 5S PCR pair; (2) SEQ ID NO.: 3 and SEQ ID NO.: 4—the 5S-SP PCR pair; and (3) SEQ ID NO.: 5 and SEQ ID NO.: 6—the noncoding repeat (NCR) PCR pair. The first primer pair (5S PCR pair) was designed based on the clones showing homology over 400 base pairs to the 5S ribosomal DNA repeat from a genomic library of *D. immitis* DNA. The second primer pair (5S-SP PCR pair) were designed to the 5S ribosomal DNA spacer region and can be used alone or in a nested relationship with the first 5S primer pair to provide additional specificity for *D. immitis*; the use of the 5S-SP PCR pair generally provides increased sensitivity in the assay. The 5S ribosomal gene is shown in FIG. 2. The location of the 5S PCR pair is indicated in FIG. 2 as S2 Primer (Forward) and S16 Primer (Reverse). The 5S PCR primer set gives a PCR product of 424 base pairs. The location of the 5S-SP primer pair is indicated in FIG. 2 as 5S Spacer Forward and Reverse 5S Spacer. The 5S-SP PCR pair gives a PCR product of 193 base pairs. This 5S-SP PCR primer pair can be used alone or in nested combination with the 5S PCR pair. The third primer pair (NCR PCR pair) was designed to the clones showing homology over a 155 base pairs region (a non-coding region of unknown function) from the same genomic library of *D. immitis* DNA; this primer set also provides specificity to *D. immitis*. This non-coding repeat sequence is shown in FIG. 3. The location of the NCR PCR pair is indicated in FIG. 3 as NCR Forward Primer and NCR Reverse Primer. The NCR PCR primer set gives a PCR product of 155 base pairs. If desired, these primers may be appropriately labeled.

Thus, one object of the present invention is to provide a PCR primer set specific for *Dirofiliaria immitis*, said primer set is (1) a first pair of oligonucleotides having the sequences given by SEQ ID NO.:1, or a derivative thereof, and SEQ ID NO.:2, or a derivative thereof; (2) a second pair of oligonucleotides having the sequences given by SEQ ID NO.:3, or a derivative thereof, and SEQ ID NO.:4, or a derivative thereof; or (3) a third pair of oligonucleotides having the sequences given by SEQ ID NO.:5, or a derivative thereof, and SEQ ID NO.:6, or a derivative thereof, wherein the primer set is effective in a PCR assay for detecting the presence of *Dirofiliaria immitis* infection in samples derived from host or vector species.

Another object of the present invention is to provide a method of detecting the presence of *D. immitis* in a sample from host or vector suspected of being infected with *D. immitis*, said method comprising the steps of:

(a) providing a sample from the host or vector suspected of being infected with *D. immitis*;

(b) treating the sample to solubilize the nucleic acids therein;

(c) forming a PCR reaction solution containing at least a portion of the solubilized nucleic acids from step (b), a PCR primer set, a mixture of nucleoside triphosphate monomers, and a DNA polymerase in a buffered solution, wherein the primer set is (1) a first pair of oligonucleotides having the sequences given by SEQ ID NO.:1, or a derivative thereof, and SEQ ID NO.:2, or a derivative thereof, or (2) a second pair of oligonucleotides having the sequences given by SEQ ID NO.:3, or a derivative thereof, and SEQ ID NO.:4, or a derivative thereof; or (3) a third pair of oligonucleotides having the sequences given by SEQ ID NO.:5, or a derivative thereof, and SEQ ID NO.:6, or a derivative thereof, (d) carrying out a polymerase chain reaction on the PCR reaction solution to amplify any *D. immitis* -specific nucleic acid which is specific for the particular primer set used to a level sufficient for detection; and (e) detecting the presence of amplified *D. immitis*-specific nucleic acid in the resulting solution which is specific for the particular primer set used;

whereby the detection of the amplified *D. immitis*-specific nucleic acid which is specific for the particular primer set used indicates that *D. immitis* is present in the host or vector.

Another object of the present invention is to provide a method of detecting the presence of *D. immitis* in a sample from host or vector suspected of being infected with *D. immitis* using a nested PCR procedure, said method comprising the steps of (a) providing a sample from the host or vector suspected of being infected with *D. immitis*;

(b) treating the sample to solubilize the nucleic acids therein;

(c) forming a first PCR reaction solution containing at least a portion of the solubilized nucleic acids from step (b), a first PCR primer set, a first mixture of nucleoside triphosphate monomers, and a first DNA polymerase in a first buffered solution, wherein the primer set is a first pair of oligonucleotides having the sequences given by SEQ ID NO.:1, or a derivative thereof, and SEQ ID NO.:2, or a derivative thereof;

(d) carrying out a first polymerase chain reaction on the first PCR reaction solution to amplify any *D. immitis*-specific nucleic acid which is specific for the first primer set used;

(e) forming a second PCR reaction solution containing at least a portion of the PCR-reacted first PCR reaction solution from step (d), a second PCR primer set, a second mixture of nucleoside triphosphate monomers, and a second DNA polymerase in a second buffered solution, wherein the second primer set is a second pair of oligonucleotides having the sequences given by SEQ ID NO.:3, or a derivative thereof, and SEQ ID NO.:4, or a derivative thereof;

(f) carrying out a second polymerase chain reaction on the second PCR reaction solution to amplify any *D. immitis*-specific nucleic acid which is specific for the second primer set used to a level sufficient for detection; and (g) detecting the presence of amplified *D. immitis*-specific nucleic acid in the resulting solution from step (f) which specific for the second primer set;

whereby the detection of the amplified *D. immitis*-specific nucleic acid which is specific for the second primer set indicates that *D. immitis* is present in the host or vector. The monomers, polymerase, and buffer components in the second PCR reaction mixture may be derived from the first PCR reaction or may be newly added to the second PCR reaction mixture or may be a combination of components from the first PCR reaction mixture and newly added components.

Still another object of the present invention is to provide a method of detecting the presence of *D. immitis* in a sample from a host or vector suspected of being infected with *D. immitis*, said method comprising the steps of (a) obtaining the sample from the host or vector suspected of being infected with *D. immitis*, (b) treating the sample to solubilize the nucleic acids therein, (c) combining all or a portion of the solubilized nucleic acids from step (b) with a buffered solution containing a mixture of a primer set designed to amplify a repeated DNA sequence from *D. immitis* genome, a mixture of nucleoside triphosphate monomers, and a DNA polymerase, whereby a PCR reaction solution is obtained;

(d) carrying out a polymerase chain reaction on the PCR reaction solution to amplify any *D. immitis*-specific nucleic acid which is specific for the primer set to a level sufficient for detection; and (e) detecting the presence of amplified *D. immitis*-specific nucleic acid in the resulting solution which is specific for the primer set;

whereby the detection of the amplified *D. immitis*-specific nucleic acid which is specific for the primer set indicates that *D. immitis* is present in the sample.

It is still another object of the present invention to provide kits suitable for carrying out the methods of the present invention.

In addition to the methods discussed above relating to the detection of parasites in blood samples, this invention is also directed to a more general method of preparing mammal blood samples whereby the DNA of organisms that may be present in the blood can be liberated for detection. Such organisms include, for example, parasites, viruses, bacteria, and the like. Thus, another object of the present invention is to provide a method of liberating DNA from the blood of a mammal or other organisms that may be present in the blood for analyzing DNA from the mammal or other organisms that may be present in the blood, said method comprising the steps of:

(a) drawing blood from the mammal;

(b) diluting at least a portion of the sample in a buffer;

(c) separating cells and other organisms from the liquid portion of the diluted sample;

(d) collecting the separated cells and other organisms; and (e) contacting the collected and separated cells and other organisms with a solution capable of disrupting the cells and other organisms under conditions and for a time sufficient to liberate DNA from the cells and other organisms;

whereby the liberated DNA is in a form suitable to be analyzed.

As one skilled in the art will realize, these and other objects and advantages of the present invention are apparent from a consideration of the present specification.

BRIEF DESCRIPTION OF THE FIGURES

FIG. 1 provides the sequences of the specific primers developed for use in this invention.

DETAILED DESCRIPTION OF THE INVENTION

Figure 2:
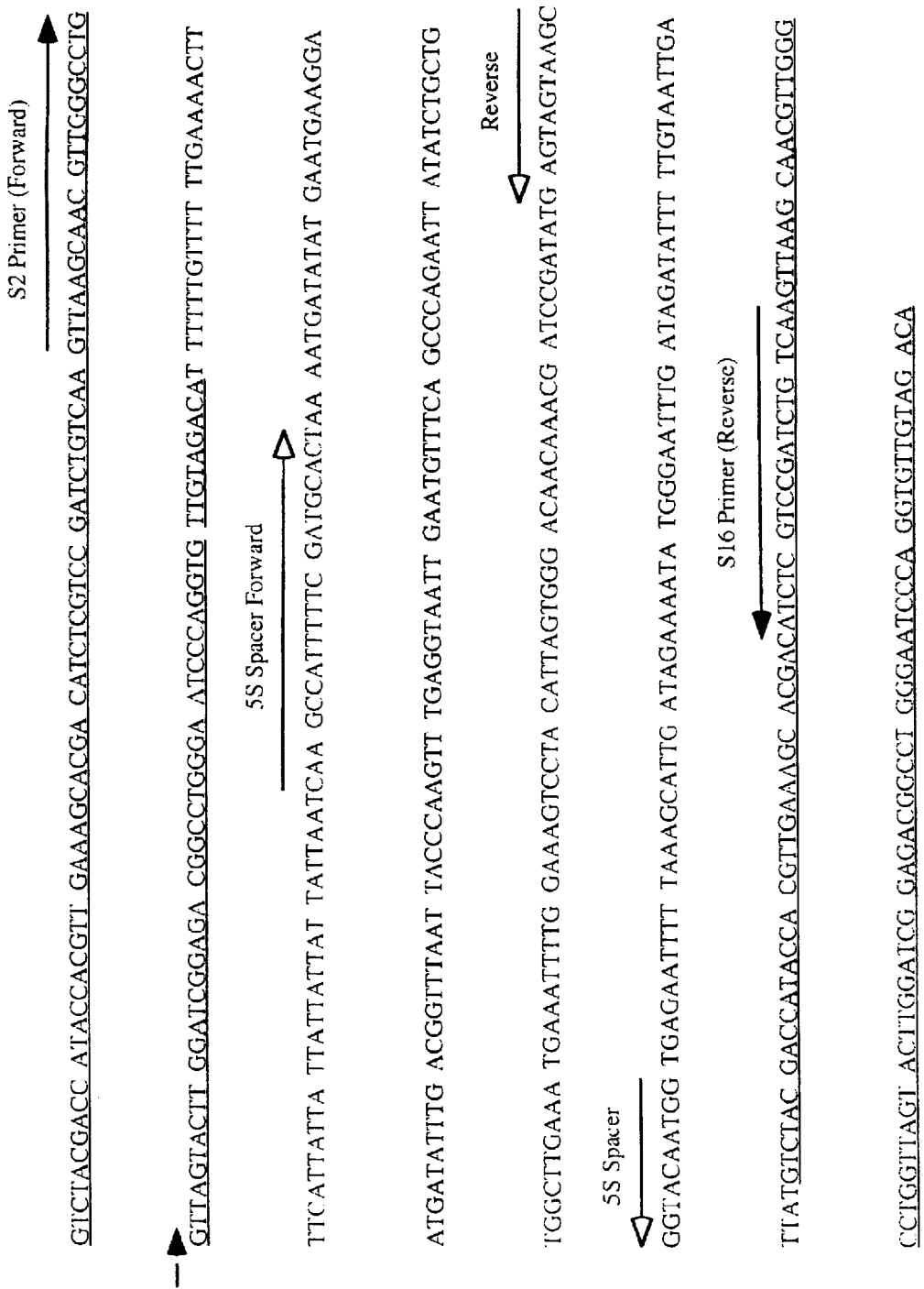
FIG. 2 provides the sequence of the 5S ribosomal gene (SEQ ID NO:7) and indicates the locations of the first 5S (i.e., S2 and S16) and second 5S-SP (forward and reverse 5S spacer) primer sets. The coding sequences are underlined.

The present invention provides PCR primers and PCR-based methods for the detection of D. immitis infection in host species (e.g., dogs, cats, or other mammals) and/or vector species (i.e., mosquitoes) using PCR techniques and the specific primer sets illustrated in FIG. 1 or derivative primer sets thereof. Using the primer sets and methods of this invention allows for detection of less than about one attogram ($10^{-18}$ grams) of D. immitis DNA, which corresponds to less than one microfilaria in 1 ml of blood or less than one L3 larva in about fifty mosquitoes. Moreover, this assay can detect D. immitis infection for all stages of the parasite and can detect prepatent infections (i.e., infections before microfilariae are produced). The present invention can detect D. immitis DNA released from microfilarae, L1, L2, L3, L4, and/or L5 (immature adults) stages, transitional stages, and/or adult worms. Such "free" DNA could be from cells sloughed off during molting or as a normal part of cell-sloughing from the surface or gut of the worms. Such DNA may also be released with excretory/secretory products from the parasite at various stages. The present methods are adapted for use in mass screening of mammalian host species (especially for dog and/or cat host species) for D. immitis infection and for geographic screening of D. immitis infection in vector mosquitoes.

As used herein the terms "polymerase chain reaction" and "PCR" relates to a procedure whereby a limited segment of a nucleic acid molecule, which frequently is a desired or targeted segment, is amplified repetitively to produce a large amount of DNA molecules which consist only of the segment. The procedure depends on repetition of a large number (generally 20 to 40) of replication cycles. In each cycle, two oligonucleotide primers bind to the segment, and define the limits of the segment. A primer-dependent DNA polymerase then replicates the strands to which the primers have bound. Thus, in each cycle, the number of DNA duplexes is doubled. PCR is well known to skilled artisans in the fields of molecular biology and genetic engineering, and is described in operational detail in, for example, "Molecular Cloning: A Laboratory Manual", 2nd Ed., Sambrook, Fritsch and Maniatis, Cold Spring Harbor Laboratory, Cold Spring Harbor, N.Y., 1989; "Current Protocols in Molecular Biology," Ausubel et al., Green Publishing Associates and Wiley-Interscience (John Wiley and Sons, N.Y. 1987) (updated quarterly); and U.S. Pat. No. 4,965,188, each of which are incorporated herein by reference.

As used herein the term "primer" or "oligonucleotide primer" relates to an oligonucleotide having a specific or desired nucleotide sequence which is complementary to a particular sequence on one of the strands of a DNA duplex. When the primer is caused to hybridize to the specific sequence in a DNA duplex to which it is complementary, it may serve as the priming position, or the initiation position, for the action of a primer-dependent DNA polymerase activity. The primer, once hybridized, acts to define one end of the operation of the replication activity of the polymerase on the duplex. By employing a specific pair of primers, one for each strand, such that replication in each is in the direction leading to the site of hybridization of the second primer to the second strand of the duplex, the specific primer pair limits a sequence in a DNA duplex in a PCR amplification procedure to produce a defined segment.

The "DNA polymerase" used in the present invention can be any of the known DNA polymerase enzymes. Examples of such enzymes include, but are not limited to, the Taq series of PCR enzymes from Perkin-Elmer Corporation, (Foster City, Calif.) and the like. An especially preferred PCR enzyme is Taq Gold™ Polymerase from Perkin-Elmer. The PCR protocols presented in the present specification are based on the use of Taq Gold™ Polymerase. As one of ordinary skill in the art will realize, the use of other PCR enzymes may required appropriate modification of the PCR protocols and reagents to take into account the specific characteristics of the enzyme used. Such modifications are within the level of ordinary skill in the art.

The preferred "primers" and/or "primer sets" of the present invention are those listed in FIG. 1. As those skilled in the art realize, modified primers and primer sets based on the "primers" and "primer sets" of FIG. 1 where the 5' ends of the primer are modified (i.e., by the addition of nucleotides and/or the deletion of a few nucleotides and/or the incorporation of labels) can also be used so long as the modifications do not significantly affect the performance of the resulting primers in the PCR reaction. Thus, for purposes of this invention, "derivatives" of the primers and/or primer sets of FIG. 1 is intended to include such modifications of the 5'-end of the primers and primer sets illustrated in FIG. 1. These "derivative primers" are also intended to include primers as shown in FIG. 1 (including those with modifications at the 5'-ends as just described) which have been chemically modified. Nonlimiting examples of such chemically modified primers include, for example, phosphorothioate derivatives, wherein a sulfur has been substituted on the α-phosphate group, and primers wherein at least one of whose bases has been modified so that it bears a particular substituent. Such a substituent may also serve as a label.

For purposes of this invention, "primers" and "primer sets" are also intended to include oligonucleotides having a specific or desired nucleotide sequence which is complementary to a particular sequence between the S2 (forward) and S16 (reverse) primers (i.e., based on 5S ribosomal gene; see FIG. 2). Preferably such primers and primer sets are selected so as to be about 18 to 25 nucleotides in length; more preferably such primers and primer sets are selected to provide PCR products of about 150 base pairs or higher and to contain about 50 percent G/C and A/T pairs.

As used herein the term "label" relates to a chemical substituent introduced into a nucleotide, an oligonucleotide primer, or a nucleic acid, and which can be detected by appropriate chemical or physical techniques. As used herein in the context of the PCR amplification procedure, a label present in a nucleotide monomer or in an oligonucleotide primer is incorporated into the amplified nucleic acid by the action of the polymerase activity. The nucleic acid product thereby bears the same label as the labeled monomer or primer substrate. Nonlimiting examples of labels include $^{32}P$ incorporated into nucleotide monomers, $\alpha\text{-}^{35}S$-phosphorothioate nucleotide monomers, biotin, fluorescein, and digoxigenin.

In the present invention, polymerase chain reaction-based diagnostic tests were developed using repeated DNA sequences that were cloned and sequenced from the dog and cat heartworm parasite *Dirofilaria immitis*. Specific PCR primers were designed to amplify these repeated DNA sequences found in the parasite genome. The following procedures were developed to use the PCR assay of the present invention. First, blood or mosquito samples containing *D. immitis* DNA and/or the *D. immitis* parasites (all stages including microfilariae; L1, L2, L3, L4, and L5 larvae; transitional stages; and adults) are processed such that structures of the worms and, in particular, the parasite surface and cells, are disrupted by solubilizing membranes and digesting proteins. As a consequence of this procedure, the parasite DNA is liberated. Next, the solubilized parasite DNA is amplified using the *D. immitis*-specific primers or the appropriate derivatives of the *D. immitis*-specific primers in the polymerase chain reaction. Third, the amplified DNA sample is detected. One method of detection for the amplified DNA sample is gel electrophoresis to size separate the amplified DNA sample for visualization using an appropriate technique (e.g., ethidium bromide, SYBR Green, or silver staining). Of course, other appropriate methods for detection of the amplified DNA sample may also be used if desired. Only those samples containing parasite DNA give a positive signal in this assay. The present method, especially when using the 5S-SP primer set alone (i.e., SEQ ID NO.3 and SEQ ID NO.4 (or their derivatives)) or the nested PCR format (i.e., using SEQ ID NO.:1 and SEQ ID NO.:2 (or their derivatives) as primers in the first PCR reaction and then using SEQ ID NO.:3 and SEQ ID NO.4 (or their derivatives) as primers in the second or nested PCR reaction), is sensitive enough to detect less than about one attogram ($10^{-18}$ grams) of *D. immitis* DNA, which corresponds to less than one microfilaria in 1 ml of blood or less than one L3 larva in about fifty mosquitoes. Surprisingly, the sensitivity of 5S-SP primer pair alone is just as good as, and sometimes better, than that of the nested pair. This increased sensitivity of the 5S-SP primer pair was first observed with the number of PCR cycles was increased from 30 to 40.

The present assay method can be used for the diagnosis of *D. immitis* infection in host species (i.e., mammals and especially dogs and cats) as well as mass screening of such host populations. The present assay method can also be used in monitoring the progress of treatment in infected host species. The present assay method can also be used in screening of mosquito populations to determine parasite transmission levels and the effectiveness of *D. immitis* eradication programs. The present assay method as applied to mosquito populations can also provide early warning of the entry of *D. immitis* infected mosquitoes into areas that were previously *D. immitis*-free.

In describing the procedures used in the practice of the invention, methods are employed which are widely known among workers of skill in the fields of molecular biology and genetic engineering. These methods are described, for example, in "Molecular Cloning: A Laboratory Manual," 2nd Ed., Sambrook, Fritsch and Maniatis, Cold Spring Harbor Laboratory (Cold Spring Harbor, N.Y., 1989) and "Current Protocols in Molecular Biology," Ausubel et al., Green Publishing Associates and Wiley-Interscience (John Wiley and Sons, N.Y. 1987) (updated quarterly).

A genomic library of *D. immitis* DNA was constructed using complete Sau3A (New England Biolabs, Beverly, Mass.) digested *D. immitis* DNA. The fragments were then ligated into the bacteriophage vector M13mp18 (New England Biolabs) that had been cut with Bam HI (New England Biolabs) and was used to transform *E. coli* cells. The resulting vector library was screened with total genomic *D. immitis* DNA prepared by labeling with $\alpha\text{-}^{35}S$-dATP (Amersham, Arlington Heights, Ill.). This method of hybridizing the genomic library with labeled total genomic DNA from the original organism allows rapid identification of the most highly represented repeated DNA sequences, for they give the darkest spots on the autoradiograms. Many clones were identified, plaque purified, and single stranded (ss) M13 DNA from each purified clone was prepared. The ssM13 DNA from each clone was diluted, and equal amounts were spotted onto dot blot filters and hybridized with radioactively-labeled *D. immitis* total genomic DNA.

The clones which gave the darkest signals from the dot blots were sequenced. DNA sequences resulting from all the clones were compared. Several clones showed significant sequence identity over a 155 base pair region which is a non-coding high copy number repeat (NCR) of unknown function. Other clones showed a high proportion of identity over 400 base pairs to the 5S ribosomal DNA repeat (5S rDNA). Primers for use in the polymerase chain reaction were designed as complements to both the repeated rDNA and the NCR sequences (SEQ ID NOs.: 1, 2, 5, and 6; see FIG. 1). Additionally a pair of primers targeted to the 5S rDNA spacer region (5S-SP; SEQ ID NOs.: 3 and 4; see FIG. 1) were designed to increase sensitivity of the 5S rDNA PCR assay by use in a nested PCR assay with the 5S primers (SEQ ID NO.1 and SEQ ID NO.2) or alone in a non-nested PCR assay. Nested PCR techniques are described in, for example, Ashbaugh et al. (1997), "Specific Detection of Shedding and Latency of Bovine Herpervirus 1 and 5 Using a Nested Polymerase Chain Reaction," *J Vet. Diagn. Invest.*, 9(4): 387–394; Stiles et al. (1997), "Comparison of Nested Polymerase Chain Reaction, Virus Isolation, and Fluorescent Antibody Testing for Identifying Feline Herpesvirus in Cats with Conjunctivitis," *Anm. J. Vet. Res.*, 58(8): 804–807; Gilbert et al. (1997), "Detection of *Equine arteritis* Virus in the Semen of Carrier Stallions by Using a Sensitive Nested PCR Assay," *J. Clin. Microbiol.*, 35(8): 2181–2183; Miwa et al. (1997), "Most Probable Numbers of Enterotoxigenic *Clostridium perfingens* in Intestinal Contents of Domestic Livestock Detected by Nested PCR," *J. Vet. Med. Sci.*, 59(7): 557–560; Wen et al. (1997), "Comparison of Nested PCR with Immunofluorescent-Antibody Assay for Detection of *Ehrlichia canis* Infection in Dogs Treated with Doxycycline," *J. Clin. Microbiol.*, 35(7): 1852–1855; Stiles et al. (1997), "Use of Nested Polymerase Chain Reaction to Identify Feline Herpesvirus in Ocular Tissue from Clinically Normal Cats and Cats with Corneal Sequestra or Conjunctivitis," *Am. J. Vet. Res.*, 58(4): 338–342; Barlough et al. (1997), "Nested Polymerase Chain Reaction for Detection of *Ehrlichia risticii* Genomic DNA in Infected Horses," *Vet. Parasitol.*, 68(4): 367–373; Gamble et al. (1997), "Development of a Nested PCR. Assay for Detection of Feline Infectious Peritonitis Virus in Clinical Specimens," J. Clin. Microbiol., 35(3): 673–675; and Miwa et al. (1997), "Most Probable Number Combined with Nested Polymerase Chain Reaction for Detection and Enumeration of Enterotoxigenic *Clostridium perfingens* in Intestinal Contents of Cattle, Pig and Chicken," *J. Vet. Med Sci.*, 59(2): 89–92. The pair of primers targeted to the 5S rDNA spacer region (5S-SP; SEQ ID NOs.: 3 and 4; see FIG. 1) were designed to be used either in a nested PCR assay or alone.

After the PCR amplification is completed, the presence of any *D. immitis*-specific DNA in the resulting sample is detected. Using the 5S primer set, a PCR product of about 424 base pairs indicates the presence of *D. immitis* infection. Using the 5S-SP primer set (either alone or in a nested combination with the first primer set), a PCR product of about 193 base pairs indicates the presence of *D. immitis* infection. (Using the 5S-SP primer set with cat blood samples can result in amplification of cat DNA; the cat amplification product is sufficiently removed (at around 900 base pairs) that there is no confusion with the 193 base pair *D. immitis* amplification product.) Using the third primer set, a PCR product of about 155 base pairs indicates the presence of *D. immitis* infection.

Figure 4:
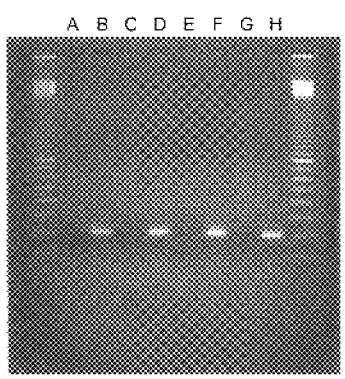
FIG. 4 illustrates the increased sensitivity obtained using the nested PCR procedure using four blood samples from dogs with prepatent (adult only) D. immitis infection. Lanes A, C, E, and G are single PCR assays using the 5S primer set; no PCR product is seen at 424 base pairs. Lanes B, D, F, and H are from nested PCR runs using 1 µl of the PCR products from lanes A, C, E, and G, respectively, with the 5S-SP primer set; a PCR product at 193 base pairs is evident indicating D. immitis infection. Markers (100 base pair ladder) are shown on the outside lanes of the agarose gel (ethidium bromide stain).
Figure 6:
FIG. 6 illustrates the detection of D. immitis infection using the third primer set. Seven dog blood samples were assayed using PCR with the third primer set. Lanes A–D and F–G were from non-infected subjects; non-infection is confirmed by the lack of a characteristic PCR product. Lane E was from an infected subject and shows the characteristic PCR product at 155 base pairs. Markers (100 base pair ladder) are shown on the left-hand side of the agarose gel (ethidium bromide stain).
Figure 5:
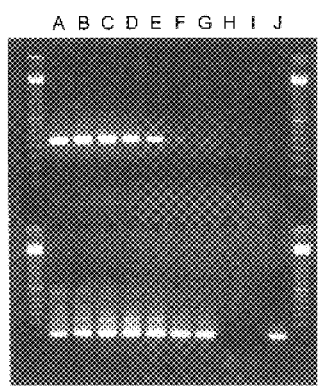
FIG. 5 illustrates the sensitivity of primer pairs associated with the 5S ribosomal gene in detecting D. immitis DNA. The PCR reactions shown in each lane were initiated with decreasing amounts of D. immitis DNA: A—1 nanogram; B—100 picograms; C—10 picograms; D—1 picogram; E—100 femtograms; F—10 femtograms; G—1 femtogram; H—100 attograms; I—10 attograms; and J—1 attograms. The top gel shows PCRs (total volume 25 µl) using the 5S primer set. The bottom gel shows nested PCR using 1 µl of the PCR product from the 5S primer set PCR with the 5S-SP primer set. The 5S primer set PCR (top gel) shows a clear single band at 424 base pair and is able to detect D. immitis DNA in the femtogram range. The nested PCR (bottom gel) shows a distinct band at 193 base pairs and is able to detect D. immitis DNA in the attogram range. Markers (100 base pair ladder) are shown on the outside lanes of the agarose gel (ethidium bromide stain).

The detection of the *D. immitis*-specific DNA may be carried out in a variety of ways. For example, the amplified nucleic acid samples may be run in agarose gel electrophoresis to segregate the product by size, and then the DNA visualized with a dye such as the fluorescent DNA-binding dye ethidium bromide. FIGS. 4–6 illustrate the use of an agarose gel electrophoresis with ethidium bromide staining. Other suitable gels (e.g., polyacrylamide) may also be used to size-select, and visualize, the amplified nucleic acid products. Alternatively, a variety of labels may be incorporated into the amplified nucleic acid product. If the label is radioactive, such as $^{32}P$ or $^{35}S$, the product may be detected by its radioactivity using, for example, scintillation counting or exposure to a film. The label may be biotin, in which case the biotin-labeled nucleic acid is detected using avidin or streptavidin which itself is conjugated to a label which can be, for example, an enzyme that develops a colored product or chemiluminesces when appropriate substrates are added. Commonly used conjugated enzymes include alkaline phosphatase and horseradish peroxidase. An additional example of a label is digoxigenin, which is detected with a digoxigenin-specific antibody. The antibody is conjugated to an enzyme label such as those just described for the case of conjugating to avidin or streptavidin. These and analogous labels are well known to workers of skill in nucleic acid chemistry, and to workers of skill in enzyme-linked solid phase assays. In addition, a recently-developed commercial solid phase assay marketed under the name DARAS™ by Tepnel Life Sciences PLC (Knutsford, UK; see Genetic Engineering News, Vol. 17, No. 20, Nov. 15, 1997, p. 1) could be used if desired. Southern blot hybridization, PCR-ELISA, or dot blot/slot blot techniques with appropriately labeled probes (e.g., NCR repeat, 5S, 5S spacer, or subsequences thereof) could also be used if desired.

The sequences of the preferred primers sets employed in the present invention are provided in FIG. 1. As indicated above, derivatives of these primers and/or primer sets may also be used. To form the derivatives, the 5'-ends of the primers can be modified in a number of ways without significantly affecting the performance of the primers in the present assay. For example, and using the specific primer identified as SEQ ID NO.:1 for illustration purposes, derivatives of the general formula

5'- (N)$_x$GTTAAGCAACGTTGGGCCTGG-3' where N represent any nucleotide and x is an integer greater than or equal to 1, could be used so long as the N tail is not so long as to significantly affect hybridization with the desired target sequences of *D. immitis* during the PCR reaction. Generally, it is preferred that N tail be less than about 20 nucleotides (i.e, x is less than about 20) in such derivatives. Suitable derivatives can also contain fewer nucleotides than that illustrated in FIG. 1 so long as the remaining nucleotide sequence (especially towards the 3'-end) retains the ability to hybridize with the desired target sequences of *D. immitis*. Again using specific primer identified as SEQ ID NO.:1 for illustration purposes, derivatives of the general formulae

5'-TTAAGCAACGTTGGGCCTGG-3'

5'-TAAGCAACGTTGGGCCTGG-3'

5'-AAGCAACGTTGGGCCTGG-3'

5'-AGCAACGTTGGGCCTGG-3' and the like may be used. In this example, nucleotides from the 5'-end of SEQ ID NO.:1 have been removed in a stepwise fashion. Since the 3'-end remains unchanged, these derivatives retain the ability to hybridize with the target *D. immitis* sequences. Of course, removal of too many of the nucleotides from the 5'-end will result in increased hybridization at non-target sequences and, therefore, result in decreased sensitivity and ultimately in false negatives. As those skilled in the art will realize, similar modifications can be made to the 3'-end. With modifications of the 3'-end, however, the length of the resulting PCR products will be changed accordingly.

Generally, it is preferred that the primer derivatives of this type retain at least 17 nucleotides, as measured from the 3' end, as the corresponding specific primer shown in FIG. 1. The shortened primer derivatives may also, if desired, have N-tails (as described above) on the 5' end so long as hybridization to the target *D. immitis* sequence is maintained. And as one of ordinary skill in the art will realize, other similar derivatives of the primers shown in FIG. 1 could also be used. For example, derivatives primers could be used in which nucleotides matching the target *D. immitis* sequences are added at the 5' and/or 3' ends or are added at one of the ends and removed from the other. Likewise, derivatives primers could also be used which are derived from the derivatives in FIG. 1 by simply moving up or downstream along the target sequences shown in FIGS. 2 and 3. Generally, it is preferred that the primer derivatives of this type retain at least 17 nucleotides matches. Although some of these derivatives have been illustrated using SEQ ID NO.:1, it should be understood that the other primers in FIG. 1 may have similar derivatives. Generally, the specific primer sequences as shown in FIG. 1 are preferred in the practice of this invention since they provide excellent sensitivity and specificity.

As noted earlier, the blood sampling techniques of this invention, which are described in detail in the Examples, can be used to liberate DNA from mammalian blood (including human) which may be infected with a wide variety of organisms so that the DNA can be subjected to appropriate analysis (including, for example, the detection of *D. immitis* as detailed in this specification). Generally, parasites are more difficult to break up (i.e., liberate the DNA contained therein) that other organisms (including virus, bacteria, and the like) that may be present in the mammalian blood. Thus, the present method, which is capable of liberating DNA from parasites such as *D. immitis,* should also liberate DNA from other organisms that may be present. Thus, the present method for treating blood is useful for liberating DNA from a wide variety of infectious organisms. Using suitable detection techniques specific for the DNA from such infectious organism, a screening technique for a wide variety of infectious organism may be developed. Thus, it is anticipated that the present blood sampling technique may be used for large scale screening protocols wherein the each blood sample may then be analyzed for the presence of infectious organisms.

The following examples are provided in order to illustrate particular embodiments of the present invention. They should not be construed to limit the scope of the invention from that which is described in detail in the present specification.

EXAMPLES

The following assay solutions were employed in the Examples. Specific protocols for the assay are given in the Examples below. Of course, as one of ordinary skill in the art will realize, various modifications of these solutions (both as to ingredients, concentration of ingredients, amounts, pH, and the like) and specific protocols (as to ingredients concentration of ingredients, amounts, assay conditions, and the like) can be made. The present assay solutions and protocols generally represent the optimized solutions and protocols known to the inventors at the time this application was filed.

Blood Assay Solutions:

TE Buffer (500 ml of solution):

| | |
|---|---|
| 1 M Tris, pH 8.0 | 5.0 ml |
| 0.5 M EDTA, pH 8.0 | 0.1 ml |
| $H_2O$ to 500 ml. | |
| Sterilize and store at room temperature. | |

Blood Lysis Buffer (500 ml of solution):

| | |
|---|---|
| Sucrose | 170 g |
| 1 M Tris, pH 7.6 | 5.0 ml |
| 1 M $MgCl_2$ | 2.5 ml |
| Triton X-100 | 5.0 ml |
| $H_2O$ to 500 ml. | |
| Sterilize and store at 4° C. | |

PK Stock Solution (500 ml of solution):

| | |
|---|---|
| 1 M Tris, pH 8.0 | 10.0 ml |
| 1 M KCl | 25.0 ml |
| 1 M $MgCl_2$ | 1.25 ml |
| $H_2O$ to 500 ml. | |
| Sterilize and store at room temperature. | |

PK Buffer

| | |
|---|---|
| PK Stock Solution | 979.9 µl |
| Proteinase K (10 mg/ml) | 15 µl |
| Tween 20 | 5.2 µl |
| | 1 ml |

Mosquito Assay Solutions:

MB Buffer (500 ml of solution):

| | |
|---|---|
| 5 M NaCl | 10 ml |
| 1 M Tris pH 8 | 15 ml |
| 0.5 M EDTA | 30 ml |
| β2-Mercaptoethanol | 355 µl |
| NP-40 | 26 ml |
| $H_2O$ to 500 ml. | |
| Sterilize and store at room temperature. | |

GT1 Buffer

| | |
|---|---|
| Guanidine Thiocyanate | 120 g |
| 0.1 M Tris, pH 6.4 | 100 ml |
| Dissolve at 65° C. then add: | |
| Triton X-100 | 2.7 g |
| EDTA 0.2 M pH 8 | 22 ml |

Mosquito Lysis Solution (for 100 ml of solution)

| | |
|---|---|
| 0.2 M NaOH | 50.5 ml |
| SDS 10% | 2.1 ml |
| $H_2O$ to 100 ml | |
| Autoclave and store at room temperature. | |

GT2 Buffer

| | |
|---|---|
| Guanidine Thiocyanate | 120 g |
| 0.1 M Tris, pH 6.4 | 100 ml |
| Dissolve at 65° C. | |
| Autoclave and store at room temperature. | |

Activated Silica Solution:

(a) Remove fines by allowing 60 grams of silica to settle in 500 ml of $H_2O$ overnight. Remove 400 ml of suspension and repeat.
(b) Remove the top 440 ml of the settled suspension. Transfer the remaining 60 ml of the suspension to a 250 ml bottle. Add 10 drops of concentrated (12 N) HCl to activate the silica (i.e., so that it binds DNA).
(c) Autoclave the suspension, and transfer to a sterile 50 ml tube.

Example 1

This example illustrates the general procedures used to identify the specific primer sets contained in FIG. 1. A genomic library of *D. immitis* DNA was constructed using complete Sau3A (New England Biolabs, Beverly, Mass.) digested *D. immitis* DNA. The fragments were then ligated into the bacteriophage vector M13mp18 (New England Biolabs) that had been cut with BanHI (New England Biolabs) and was used to transform *E. coli* cells. The resulting vector library was screened with total genomic *D. immitis* DNA prepared by labeling with α-$^{35}$S-dATP (Amersham, Arlington Heights, Ill.). This method of hybridizing the genomic library of the clones with labeled total genomic DNA from the original organism allows rapid identification of the most highly represented repeated DNA sequences, for they give the darkest spots on the autoradiograms. Many clones were identified, plaque purified, and single stranded (ss) M13 DNA from each purified clone was prepared. The ssM13 DNA from each clone was diluted, and equal amounts were spotted onto dot blot filters and hybridized with radioactively-labeled *D. immitis* total genomic DNA.

Figure 3:
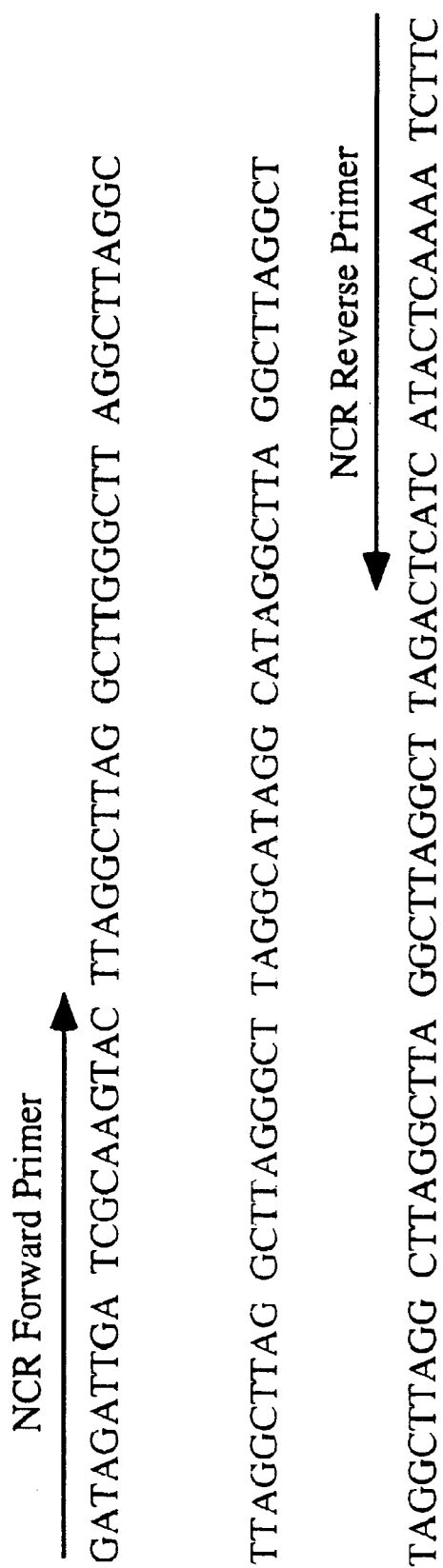
FIG. 3 provides the sequence of the non-coding repeat (NCR) (SEQ ID NO:8) and indicates the locations of the third primer set.

The clones which gave the darkest signals from the dot blots were sequenced. DNA sequences resulting from all the clones were compared. Several clones showed significant sequence identity over a 155 base pair region which is a non-coding repeat (NCR) of unknown function. Other clones showed a high proportion of identity over 400 base pairs to the 5S ribosomal DNA repeat (5S rDNA). The sequence for the 5S ribosomal DNA repeat is shown in FIG. 2. The sequence for the NCR region is shown in FIG. 3. Using these sequences, primers for use in the polymerase chain reaction were designed as complements to both the repeated rDNA and the NCR sequences (SEQ ID NOs.: 1, 2, 5, and 6; see FIGS. 1, 2, and 3). Additionally a pair of primers targeted to the 5S rDNA spacer region (5S-SP; SEQ ID NOs.: 3 and 4; see FIGS. 1 and 2) were designed to increase sensitivity of the 5S rDNA PCR assay. The 5S-SP primer set can be used alone or in nested combination with the 5S primer set. Primers were generally selected so as to be about 18 to 25 nucleotides in length, to contain about 50 percent G/C and A/T pairs, and to provide PCR products of about 150 base pairs or higher. For the 5S rDNA spacer primer set (i.e., 5S-SP), the *D. immitis* 5S gene sequence was compared to about 15 other filarial parasite 5S genes; the PCR primers were selected from a region which was found to be the most different as compared to the other parasites in order to obtain a high degree of species-specificity.

Example 2

This example illustrate the sample preparation portion of the assay of the present invention using blood samples of dogs suspected of being infected by *D. immitis*. After collection using standard techniques, the blood samples were prepared and processed using the following protocol:

(a) Blood samples should be collected in EDTA vacutainers and mixed well immediately. Soon after collection in the EDTA vacutainers, 1 ml blood is mixed with 2.5 ml of 0.002% SDS; if samples are not to be analyzed immediately, they should be frozen. For testing, 1.5 ml of the blood/SDS sample is added to a 1.7 ml microfuge tube.

(b) Centrifuge the samples for 2 minutes at 16,500×g to pellet parasite material and blood cells, and rinse the pellet twice with TE and twice with Blood Lysis Buffer.

(c) Add 200 μl of prewarmed (65° C.) PK Buffer (containing proteinase K) to the pellet and digest the samples in a water bath at 65° C. for 2 hours with occasional vortexing.

(d) Heat samples at 90–95° C. for 10–15 minutes to inactivate Proteinase K. The resulting solution contains DNA derived from any *D. immitis* parasites that might have been present in the blood sample.

Example 3

This example illustrates the sample preparation portion of the assay of the present invention using samples derived from mosquitoes suspected of being infected by *D. immitis* (especially the L3 infective larvae stage). After collection of the suspected mosquitoes using standard techniques, samples were prepared and processed using the following protocol:

(a) Dry 1–50 mosquitoes in a 1.5 ml microfage tube for about 3.2 hours at 90–92° C.

(b) Crush dry mosquitoes with a sterile plastic pestle. Extract twice with 1 ml of MB buffer.

(c) Add 100 μl of 0.1 M NaOH, 0.2% SDS to each tube. Incubate at 37° C. for about 2 hour to lyse L3 worms.

(e) Neutralize the samples by adding 5 μl 2 M HCl.

(f) Add 1 ml of GT1 buffer and 40 μl of activated silica to each sample.

(g) Incubate at room temperature for 10 minutes, then centrifuge.

(h) Wash silica pellet 2 times with 1 ml GT2 buffer and 2 times using 1 ml 70% ethanol.

(i) After drying the pellet, resuspend it in 100 μl TE pH 8.

(j) Incubate samples for 10–11 minutes at 56° C. to elute DNA from the silica, and centrifuge.

The resulting supernatant contains DNA derived from any *D. immitis* parasites that might have been present in the mosquito sample.

Example 4

This example illustrates the PCR portion of the assay using DNA samples from Examples 2 or 3 and using the primer set consisting of SEQ ID NO.: 1 and SEQ ID NO.:2. Detection of PCR-amplified product can be, for example, carried out with gel electrophoresis and ethidium bromide staining.

The DNA sample obtained in Example 2 or 3 were further treated using the following sample preparation protocol:

A 2 μl aliquot of the DNA sample from the lysate is combined with:

5.0 μl 10×PCR Buffer 12.0 μl dNTPs (a mixture of the four deoxynucleoside triphosphates of A, C, T, and G)

6.0 ml MgCl$_2$ (25 mM)

1.0 μl *D. immitis* Forward Primer (20 pmol/μl) (SEQ ID NO.:1)

1.0 μl *D. immitis* Reverse Primer (20 pmol/μl) (SEQ ID NO.:2)

28.5 μl H$_2$O 0.5 μl Taq Gold™ Polymerase (Perkin-Elmer, Foster City, Calif.)

50.0 μl (total volume)

to form the PCR samples. The PCR samples are then placed in a thermal cycler instrument (Perkin-Elmer, Foster City, Calif.). Conventional PCR is carried out using the following PCR thermal cycle program:

95° C. for 12 minutes 30 cycles of

95° C. for 30 seconds

60° C. for 30 seconds

72° C. for 30 seconds

72° C. for 10 minutes.

Once the 30 cycles are completed, the samples are held at low temperatures (i.e., about 4° C.) until visualization.

Following the thermal cycling, about 10.0 μl of each sample is electrophoresed on a 2.5% agarose gel using 1X TAE buffer. The gel is stained with ethidium bromide and photographed on an ultraviolet illumination instrument.

Example 5

This example illustrates the use of nested PCR the 5S primer set (SEQ ID NO.:1 and SEQ ID NO.:2) followed by PCR using the 5S-SP primer set (SEQ ID NO.:3 and SEQ ID NO.:4). The use of the nested PCR procedure or the 5S-SP primer set alone allows for even greater sensitivity and species specificity.

Following the first PCR procedure as described in Example 4, a second (nested) PCR is performed using the 5S PCR product as the template. Essentially the same protocol as used in Example 4 is used except that primer set used is the 5S-SP pair (SEQ ID NO.:3 and SEQ ID No.:44) and the thermal cycling protocol is modified as follows:

95° C. for 12 minutes
40 cycles of:
   95° C. for 1 minute
   57° C. for 1 minute
   72° C. for 1 minute
   72° C. for 10 minutes.

Once the 40 cycles are completed, the samples are held at low temperatures (i.e., about 4° C.) until visualization.

A nested PCR assay with prepatent dog blood samples is shown in FIG. 4. In these samples, only adult worms were present. Lanes A, C, E, and G are single PCR assays (total volume 25 µl) using the first primer set (run as described in Example 4). Lanes B, D, F, and H are from nested PCR runs using 1 µl of the PCR products from lanes A, C, E, and G, respectively, with the second primer set. One-third of the total volume (about 8 µl) of each PCR was mixed with 2 µl of 5X loading dye and run on a 2.5 percent agarose gel using 1X TAE buffer; 100 base pair ladder molecular weight markers were run on the outside lanes. The gel was run for about one hour at 80 volts and then stained in an ethidium bromide staining bath (6 µl/ml dd $H_2O$) for about 5 minutes and destained about 30 minutes and then photographed on an UV light box. No PCR product is seen at 424 base pair in Lanes A, C, E, and G. A PCR product of 193 base pairs in evident in Lanes B, D, F, and H. Thus, using the nested PCR procedure of this invention, prepatent infection can be readily detected.

A second nested PCR assay with varying amounts of added *D. immitis* DNA is illustrated in FIG. 5. Each lane of FIG. 5 represents a PCR reaction with decreasing amounts of *D. immitis* DNA added as template: A—1 nanogram; B—100 picograms; C—10 picograms; D—1 picogram; E—100 femtograms; F—10 femtograms; G—1 femtogram; H—100 attograms; I—10 attograms; and J—1 attogram. The top get shows PCRs (total volume 25 µl) using the first primer set. One-third of the total volume (about 8 µl) of the initial PCR was mixed with 2 µl of 5xloading dye and run on a 2.5 percent agarose gel using 1xTAE buffer; 100 base pair ladder molecular weight markers were run on the outside lanes. The gel was run for abut one hour at 80 volts and then stained in an ethidium bromide staining bath for about 5 minutes and destained about 30 minutes and then photographed on an UV light box. The bottom gel shows nested PCR using 1 µl of the PCR product from the first primer set PCR with the second primer set. The bottom gel was obtained in the same manner as the top gel. The first primer set PCR (top gel) shows a clear single band at 424 base pair and is able to detect *D. immitis* DNA in the femtogram range. The nested PCR (bottom gel) shows a distinct band at 193 base pair and is able to detect *D. immitis* DNA in the attogram range.

Example 6

Figure 7:
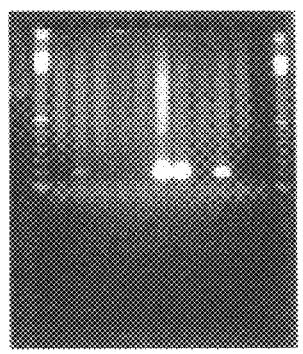
FIG. 7 illustrates the use of the 5S-SP primer pair used alone in detecting D. immitis DNA. Ten dog blood samples were assayed using PCR with the 5S-SP primer set. Lanes A, C, D, E, H, and J were from non-infected subjects; non-infection is confirmed by the lack of a characteristic PCR product. Lanes B, F, G, and I were from infected subjects and shows the characteristic PCR product at distinct band at 193 base pairs. Markers (100 base pair ladder) are shown on the outside lanes of the agarose gel (ethidium bromide stain).

This example illustrates the use of the 5S-SP primer set alone. The same procedures and protocols as in Example 5 for the 5S-SP primer set were used. In other words, only the procedures and protocols for the 5S-SP primer set as detailed in Example 5 were used. Ten dog blood samples were assayed using PCR with only the 5S-SP primer set. The results are shown in FIG. 7. Lanes A, C, D, E, H, and J were from non-infected subjects; non-infection is confirmed by the lack of a characteristic PCR product. Lanes B, F, G, and I were from infected subjects and shows the characteristic PCR product at distinct band at 193 base pairs. Markers (100 base pair ladder) are shown on the outside lanes of the agarose gel (ethidium bromide stain).

Example 7

This example illustrates the PCR portion of the assay using DNA samples from Examples 2 or 3 and using the primer set consisting of SEQ ID NO.:5 and SEQ ID NO.:6. Detection of PCR-amplified product can be, for example, carried out with gel electrophoresis followed with staining with ethidium bromide. Samples from Examples 2 and 3 are first treated using the same sample preparation protocol as described in Example 4. PCR is then carried out as described in Example 4 except that primer pair used is the NCR DNA pair (SEQ ID NOs.: 5 and 6) instead of SEQ ID NOs. 1 and 2, and the thermal cycling protocol is that shown above in Example 5.

FIG. 6 illustrates the detection of *D. immitis* infection using dog blood samples using the third primer set based on the non-coding repeat region. Of the seven blood samples in FIG. 6, only one was infected with *D. immitis*. Lanes A–D and F–G were from non-infected subjects; non-infection is confirmed by the lack of a PCR product. Lane E was from an infected subject and shows the PCR product at 155 base pairs.

Example 8

This example illustrates a PCR-ELISA method of detection which can be used to test 96 samples simultaneously in a microtiter plate format. This method has also been optimized for the detection of the PCR product and provides slightly better sensitivity. Although this method is more time-consuming and costly than agarose gel electrophoresis, it may be used to advantage when large number of samples are to be analyzed. The protocol follows:

(a) Coat a microtiter plate with 1 mg/ml streptavidin in SB (streptavidin buffer; 0.1M $Na_2CO_3$—$NaHCO_3$, pH 9.6). Leave at 4° C. for a minimum of 7.5 hours (coated plates can be stored for two weeks at 4° C.).

(b) Discard streptavidin solution and wash wells of plate twice with 100 ml of 2×PBS (for all washing steps, stamp plate vigorously on paper towels to get all solution out of the wells).

(c) Mix 16 µl of each PCR product with 84 µl of hybridization buffer (6×SSPE, 5×Denhardts, 0.1% sodium sarcosine, 0.02% SDS, 0.05% $NaN_3$). Add 100 µl of sample to separate wells of coated microtiter dish, cover, and incubate at room temperature for 35 minutes.

(d) To each well of microtiter plate add 100 µl of 0.3M NaOH and incubate plate at room temperature for 11 minutes.

(e) Discard solution in dish, and wash wells with 100 µl of 1×PBS followed by 100 µl of hybridization buffer.

(f) Dilute fluoresceinated hybridization probe (derived from the sequence of the PCR products) to 50 pg/ml in hybridization buffer. Denature probe at 94° C. for 7 minutes then snap cool on ice for 5 minutes. One suitable probe sequence with two fluorescein molecules for the 5S-SP PCR product is shown below:

5'- FL*-ATC TGC TGT GGC TTG AAA TGA AAT-FL*-3'

(g) Add 100 µl of probe to each well of microtiter dish, seal with plastic plate sealer and incubate plate at 55° C. for 30 minutes.

(h) Wash wells of plate twice with 100 µl of 1×PBS at room temperature followed by once with 100 µl of PBS/ 0.5% BSA at 55° C.

(i) Dilute Anti-Fluorescein FAB fragment conjugated to alkaline phosphatase (Boehringer-Mannheim) 1:3000 in PBS/0.5% BSA. Add 100 µl of diluted antibody to each well of microtiter plate, seal plate, and incubate at 37° C. for 33 minutes.

(j) Wash wells of plate three times with 100 µl 1×PBS/ Tween and twice with assay buffer (1% diethanolamine, 20 mM $MgCl_2$, pH 10).

(k) Add 3 tablets of phosphatase substrate (Sigma 104) to 15 ml of alkaline phosphatase buffer (Sigma) and dissolve tablets. Add 100 µl of substrate to each well of microtiter dish, seal plate, and incubate at 37° C. for 1–2 hours. Read plate in ELISA reader at 405 nm.

The hybridization probe, derived from the PCR product produced using the 5S-SP primer set, was selected on the basis of its hybridization properties (i.e., a good mix of A, G, C, and T; no long runs of any particular nucleotide; no internal hybridization to form hairpins, and the like). Of course, other hybridization probes could also be selected using the same criteria from within the 5S, 5S-SP, or NCR PCR products. Indeed, the entire 5S ribosomal sequence in FIG. 2 (434 bases) can be used as a hybridization probe. The use of the entire 434 base pair sequence is sensitive, but not species-specific. Furthermore, the entire 5S-SP region (or derivatives thereof) within the ribosomal gene (bases 121 to 434) can be used as a species-specific probe for D. immitis. Derivatives thereof could include shorter regions within the 434 base pair sequence. Moreover, other labels (e.g., biotin, digoxigenin, $^{32}P$, and the like) could be used on the probe if desired.

We claim:

1. A PCR primer set specific for *Dirofiliaria immitis,* said primer set is (1) a first pair of oligonucleotides having the sequences given by SEQ ID NO.:1, or a derivative thereof, and SEQ ID NO.:2, or a derivative thereof, (2) a second pair of oligonucleotides having the sequences given by SEQ ID NO.:3, or a derivative thereof, and SEQ ID NO.:4, or a derivative thereof, or (3) a third pair of oligonucleotides having the sequences given by SEQ ID NO.:5, or a derivative thereof, and SEQ ID NO.:6, or a derivative thereof, wherein the primer set is effective in a PCR assay for detecting the presence of *Dirofiliaria immitis* infection in samples derived from host or vector species.

2. A PCR primer set as described in claim 1, wherein one or both the oligonucleotides forming the primer set is labeled.

3. A PCR primer set as described in claim 1, wherein the primer set is the first pair of oligonucleotides.

4. A PCR primer set as described in claim 1, wherein the primer set is the second pair of oligonucleotides.

5. A PCR primer set as described in claim 1, wherein the primer set is the third pair of oligonucleotides.

6. A method of detecting the presence of *D. immitis* in a sample from host or vector suspected of being infected with *D. immitis,* said method comprising the steps of:
   (a) providing a sample from the host or vector suspected of being infected with *D. immitis;*
   (b) treating the sample to solubilize the nucleic acids therein;
   (c) forming a PCR reaction solution containing at least a portion of the solubilized nucleic acids from step (b), a PCR primer set, a mixture of nucleoside triphosphate monomers, and a PCR polymerase in a buffered solution, wherein the primer set is (1) a first pair of oligonucleotides having the sequences given by SEQ ID NO.:1, or a derivative thereof, and SEQ ID NO.:2, or a derivative thereof; or (2) a second pair of oligonucleotides having the sequences given by SEQ ID NO.:3, or a derivative thereof, and SEQ ID NO. :4, or a derivative thereof; or (3) a third pair of oligonucleotides having the sequences given by SEQ ID NO.:5, or a derivative thereof, and SEQ ID NO.:6, or a derivative thereof;
   (d) carrying out a polymerase chain reaction on the PCR reaction solution to amplify any *D. immitis*-specific nucleic acid which is specific for the particular primer set used to a level sufficient for detection; and
   (e) detecting the presence of amplified *D. immitis*-specific nucleic acid in the resulting solution which is specific for the particular primer set used;
   whereby the detection of the amplified *D. immitis*-specific nucleic acid which is specific for the particular primer set used indicates that *D. immitis* is present in the host or vector.

7. The method described in claim 6 wherein the sample is blood from a host.

8. The method described in claim 7 wherein treating the sample to solubilize the nucleic acids therein further comprises the steps of:
   (i) diluting at least a portion of the sample in a buffer;
   (ii) separating cells and *D. immitis,* if present, from the liquid portion of the diluted sample; and
   (iii) contacting the separated cells and *D. immitis,* if present, with a solution capable of disrupting the cells under conditions and for a time sufficient to liberate nucleic acids from the cells and *D. immitis,* if present.

9. The method as described in claim 6, wherein the primer set is the first pair of oligonucleotides having the sequences given by SEQ ID NO.:1, or a derivative thereof, and SEQ ID NO.:2, or a derivative thereof.

10. The method as described in claim 9, wherein the primer set is the first pair of oligonucleotides having the sequences given by SEQ ID NO.:1 and SEQ ID NO.:2.

11. The method as described in claim 6, wherein the primer set is the second pair of oligonucleotides having the sequences given by SEQ ID NO.:3, or a derivative thereof, and SEQ ID NO.:4, or a derivative thereof.

12. The method as described in claim 11, wherein the primer set is the second pair of oligonucleotides having the sequences given by SEQ ID NO.:3 and SEQ ID NO.:4.

13. The method as described in claim 6, wherein the primer set is the third pair of oligonucleotides having the sequences given by SEQ ID NO.:5, or a derivative thereof, and SEQ ID NO.:6, or a derivative thereof.

14. The method as described in claim 13, wherein the primer set is the third pair of oligonucleotides having the sequences given by SEQ ID NO.:5 and SEQ ID NO.:6.

15. The method as described in claim 6 wherein the detection of the presence of amplified *D. immitis*-specific nucleic acid comprises gel electrophoresis of the amplified *D. immitis*-specific nucleic acid solution and staining of the resulting gel to visualize the band of the *D. immitis*-specific nucleic acid specific for the particular primer set used.

16. The method as described in claim 15, wherein at least one of the oligonucleotides in the primer set or at least one of the nucleoside triphosphate monomers contains a label which will be incorporated into the amplified *D. immitis*-specific nucleic acid and can be used for the detection of the amplified *D. immitis*-specific nucleic acid.

17. A method of detecting the presence of *D. immitis* in a sample from host or vector suspected of being infected with *D. immitis* using a nested PCR procedure, said method comprising the steps of:
   (a) providing a sample from the host or vector suspected of being infected with *D. immitis;*
   (b) treating the sample to solubilize the nucleic acids therein;
   (c) forming a first PCR reaction solution containing at least a portion of the solubilized nucleic acids from step (b), a first PCR primer set, a first mixture of nucleoside triphosphate monomers, and a first PCR polymerase in a first buffered solution, wherein the primer set is a first pair of oligonucleotides having the sequences given by SEQ ID NO.:1, or a derivative thereof, and SEQ ID NO.:2, or a derivative thereof;
   (d) carrying out a first polymerase chain reaction on the first PCR reaction solution to amplify any *D. immitis*-specific nucleic acid which is specific for the first primer set used;
   (e) forming a second PCR reaction solution containing at least a portion of the PCR-reacted first PCR reaction solution from step (d), a second PCR primer set, a second mixture of nucleoside triphosphate monomers, and a second PCR polymerase in a second buffered solution, wherein the second primer set is a second pair of oligonucleotides having the sequences given by SEQ ID NO.:3, or a derivative thereof, and SEQ ID NO.:4, or a derivative thereof;
   (f) carrying out a second polymerase chain reaction on the second PCR reaction solution to amplify any *D. immitis*-specific nucleic acid which is specific for the second primer set used to a level sufficient for detection; and (g) detecting the presence of amplified *D. immitis*-specific nucleic acid in the resulting solution from step (f) which specific for the second primer set;

whereby the detection of the amplified *D. immitis*-specific nucleic acid which is specific for the second primer set indicates that *D. immitis* is present in the host or vector.

18. The method described in claim 17 wherein the sample is blood from a host.

19. The method described in claim 18 wherein treating the sample to solubilize the nucleic acids therein further comprises the steps of:

(i) diluting at least a portion of the sample in a buffer;

(ii) separating cells and *D. immitis*, if present, from the liquid portion of the diluted sample; and (iii) contacting the separated cells and *D. immitis*, if present, with a solution capable of disrupting the cells under conditions and for a time sufficient to liberate nucleic acids from the cells and *D. immitis*, if present.

20. The method described in claim 17, wherein the detection in step (g) comprises gel electrophoresis of the amplified *D. immitis*-specific nucleic acid solution and staining of the resulting gel to visualize the *D. immitis*-specific nucleic acid on the gel.

21. The method described in claim 17 wherein either the primers, or one or more of the monomers, or both, employed in steps (c) and (e) contains a label whereby the amplified *D. immitis*-specific nucleic acid that results in step (f) contains the label, and the detection in step (g) comprises detecting the presence of the label.

22. A method of detecting the presence of *D. immitis* in a sample from a host or vector suspected of being infected with *D. immitis*, said method comprising the steps of (a) obtaining the sample from the host or vector suspected of being infected with *D. immitis*, (b) treating the sample to solubilize the nucleic acids therein, (c) combining all or a portion of the solubilized nucleic acids from step (b) with a buffered solution containing a mixture of a primer set designed to amplify a highly repeated DNA sequence from *D. immitis* genome, a mixture of nucleoside triphosphate monomers, and a PCR polymerase, whereby a PCR reaction solution is obtained;

(d) carrying out a polymerase chain reaction on the PCR reaction solution to amplify any *D. immitis*-specific nucleic acid which is specific for the primer set to a level sufficient for detection; and (e) detecting the presence of amplified *D. immitis*-specific nucleic acid in the resulting solution which is specific for the primer set;

wherein the highly repeated DNA sequence from the *D. immitis* genome is identified from a digested genomic library of *D. immitis* DNA which is used to prepare a vector library, wherein the vector library is screened with labeled total genomic *D. immitis* DNA, whereby the highly repeated DNA sequence from the *D. immitis* genome can be identified;

whereby the detection of the amplified *D. immitis*-specific nucleic acid which is specific for the primer set indicates that *D. immitis* is present in the sample.

23. The method described in claim 22 wherein the sample is blood from a host.

24. The method described in claim 23 wherein treating the sample to solubilize the nucleic acids therein further comprises the steps of:

(i) diluting at least a portion of the sample in a buffer;

(ii) separating cells and *D. immitis*, if present, from the liquid portion of the diluted sample; and (iii) contacting the separated cells and *D. immitis*, if present, with a solution capable of disrupting the cells under conditions and for a time sufficient to liberate nucleic acids from the cells and *D. immitis*, if present.

25. The method described in claim 22, wherein the primer set is a pair of oligonucleotides having the sequences given by SEQ ID NO.:1, or a derivative thereof, and SEQ ID NO.:2, or a derivative thereof.

26. The method described in claim 25, wherein the primer set is a pair of oligonucleotides having the sequences given by SEQ ID NO.:1 and SEQ ID NO.:2.

27. The method described in claim 22, wherein the primer set is a pair of oligonucleotides having the sequences given by SEQ ID NO.:3, or a derivative thereof, and SEQ ID NO.:4, or a derivative thereof.

28. The method as described in claim 27, wherein the primer set is a pair of oligonucleotides having the sequences given by SEQ ID NO.:3 and SEQ ID NO.:4.

29. The method described in claim 22, wherein the primer set is a pair of oligonucleotides having the sequences given by SEQ ID NO.:5, or a derivative thereof, and SEQ ID NO.:6, or a derivative thereof.

30. The method as described in claim 29, wherein the primer set is a pair of oligonucleotides having the sequences given by SEQ ID NO.:5 and SEQ ID NO.:6.

31. The method described in claim 22, wherein the detection in step (e) comprises gel electrophoresis of the amplified *D. immitis*-specific nucleic acid solution and staining the resulting gel to visualize the *D. immitis*-specific nucleic acid on the gel.

32. The method described in claim 22, wherein the detection in step (e) comprises an ELISA technique with a labeled hybridization probe suitable for detecting the *D. immitis*-specific nucleic acid.

33. The method described in claim 22, wherein the highly repeated DNA sequence from *D. immitis* genome is SEQ ID NO:7 or SEQ ID NO:8.

34. The method described in claim 22, wherein the highly repeated DNA sequence from *D. immitis* genome is 5S ribosomal DNA repeat (5S) which is amplified by the primers with SEQ ID NO.:1, SEQ ID NO:2, SEQ ID NO:3, and SEQ ID NO:4 and Non-Coding Repeat (NCR) which is amplified by the primers with SEQ ID NO:5 and SEQ ID NO:6.

* * * * *

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Dirofilaria immitis primer

<400> SEQUENCE: 1
gttaagcaac gttgggcctg g                                              21

<210> SEQ ID NO 2
<211> LENGTH: 20
<212> TYPE: DNA
<213> ORGANISM: Artificial Sequence
<220> FEATURE:
<223> OTHER INFORMATION: Dirofilaria immitis primer

<400> SEQUENCE: 2
ttgacagatc ggacgagatg                                                20

<210> SEQ ID NO 3
<211> LENGTH: 21
<212> TYPE: DNA
<213> ORGANISM: Artificial Sequence
<220> FEATURE:
<223> OTHER INFORMATION: Dirfilaria immitis primer

<400> SEQUENCE: 3
caagccattt ttcgatgcac t                                              21

<210> SEQ ID NO 4
<211> LENGTH: 21
<212> TYPE: DNA
<213> ORGANISM: Artificial Sequence
<220> FEATURE:
<223> OTHER INFORMATION: Dirofilaria immitis primer

<400> SEQUENCE: 4
ccattgtacc gcttactact c                                              21

<210> SEQ ID NO 5
<211> LENGTH: 20
<212> TYPE: DNA
<213> ORGANISM: Artificial Sequence
<220> FEATURE:
<223> OTHER INFORMATION: Dirofilaria immitis primer

<400> SEQUENCE: 5
gatagattga tcgcaagtac                                                  20

<210> SEQ ID NO 6
<211> LENGTH: 21
<212> TYPE: DNA
<213> ORGANISM: Artificial Sequence
<220> FEATURE:
<223> OTHER INFORMATION: Dirofilaria immitis primer

<400> SEQUENCE: 6
gaagattttg agtatgatga g                                                21

<210> SEQ ID NO 7
<211> LENGTH: 490
<212> TYPE: DNA
<213> ORGANISM: Artificial Sequence
<220> FEATURE:
<223> OTHER INFORMATION: Dirofilaria immitis amplified region

<400> SEQUENCE: 7
gtctacgacc ataccacgtt gaaagcacga catctcgtcc gatctgtcaa gttaagcaac      60
gttgggcctg gttagtactt ggatcggaga cggcctggga atcccaggtg ttgtagacat     120
tttttgtttt ttgaaaactt ttcattatta ttattattat tattaatcaa gccatttttc     180
gatgcactaa aatgatatat gaatgaagga atgatatttg acggtttaat tacccaagtt     240
tgaggtaatt gaatgtttca gcccagaatt atatctgctg tggcttgaaa tgaaattttg     300
gaaagtccta cattagtggg acaacaaacg atccgatatg agtagtaagc ggtacaatgg     360
tgagaatttt taaagcattg atagaaaata tgggaatttg atagatattt ttgtaattga     420
ttatgtctac gaccatacca cgttgaaagc acgacatctc gtccgatctg tcaagttaag     480
caacgttggg                                                            490

<210> SEQ ID NO 8
<211> LENGTH: 155
<212> TYPE: DNA
<213> ORGANISM: Artificial Sequence
<220> FEATURE:
<223> OTHER INFORMATION: Dirofilaria immitis amplified region

<400> SEQUENCE: 8
gatagattga tcgcaagtac ttaggcttag gcttgggctt aggcttaggc ttaggcttag      60
gcttagggct taggcatagg cataggctta ggcttaggct taggcttagg cttaggctta     120
ggcttaggct tagactcatc atactcaaaa tcttc                                 155

<210> SEQ ID NO 9
<211> LENGTH: 24
<212> TYPE: DNA
<213> ORGANISM: Artificial Sequence
<220> FEATURE:
<223> OTHER INFORMATION: Dirofilaria immitis probe

<400> SEQUENCE: 9
atctgctgtg gcttgaaatg aaat                                             24